United States Patent [19]

Klaus-Ulfert

[11] Patent Number: 4,976,073
[45] Date of Patent: Dec. 11, 1990

[54] METHOD AND APPRATUS FOR MOVING A GRANULATE MATERIAL IN A DENTAL PRACTICE SITUATION

[75] Inventor: Rieger Klaus-Ulfert, Singen, Fed. Rep. of Germany

[73] Assignee: Renfert GmbH & Co., Singen, Fed. Rep. of Germany

[21] Appl. No.: 163,810

[22] Filed: Mar. 3, 1988

[30] Foreign Application Priority Data

Oct. 30, 1987 [DE] Fed. Rep. of Germany ....... 3736972

[51] Int. Cl.⁵ ................................................ B24C 3/00
[52] U.S. Cl. ........................................ 51/410; 51/427; 51/436; 51/319
[58] Field of Search ................. 51/319, 320, 410, 427, 51/436; 118/308; 239/85; 222/630; 406/134, 135, 146; 433/88, 125, 216

[56] References Cited

U.S. PATENT DOCUMENTS

| | | | |
|---|---|---|---|
| 554,300 | 2/1896 | Parker | 51/436 |
| 2,817,310 | 12/1957 | Ponzini | 406/146 X |
| 3,415,450 | 12/1968 | Hawk | 222/630 X |
| 3,436,019 | 4/1969 | Hawk | 239/85 |
| 3,442,454 | 5/1969 | Stenger et al. | 239/85 X |
| 3,631,631 | 1/1972 | Greenstein | 51/436 X |
| 4,482,322 | 11/1984 | Hain et al. | 51/436 X |
| 4,492,575 | 1/1985 | Mabille | 433/88 |
| 4,569,161 | 2/1986 | Shipman | 51/436 |

Primary Examiner—Frederick R. Schmidt
Assistant Examiner—M. Rachuba
Attorney, Agent, or Firm—Bachman & LaPointe

[57] ABSTRACT

An apparatus for moving a granulate material for use on dental prostheses comprises a container for the material, with at least one riser pipe which projects into the space in the container above the material therein and which is fixed to a support base connected to the container. With at least one metering nozzle which terminates in the interior of the container, the riser pipe is connected to an air feed means for carrying a flow of air for conveying the material from the container in the form of an air/material mixture. At least one closure member is disposed in the mixture discharge means of the apparatus. In the method of moving the granulate material, the material is mixed with compressed air and fed in the form of a mixed flow to the dental prosthesis to be operated on, wherein a flow of control air may be fed to the granulate material prior to mixing thereof with the compressed air for fluidization of that material with the control air.

44 Claims, 2 Drawing Sheets

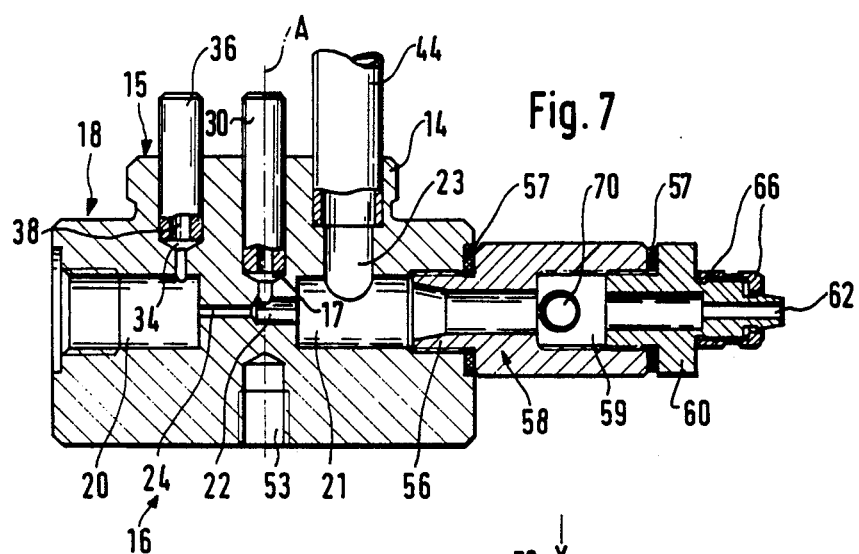
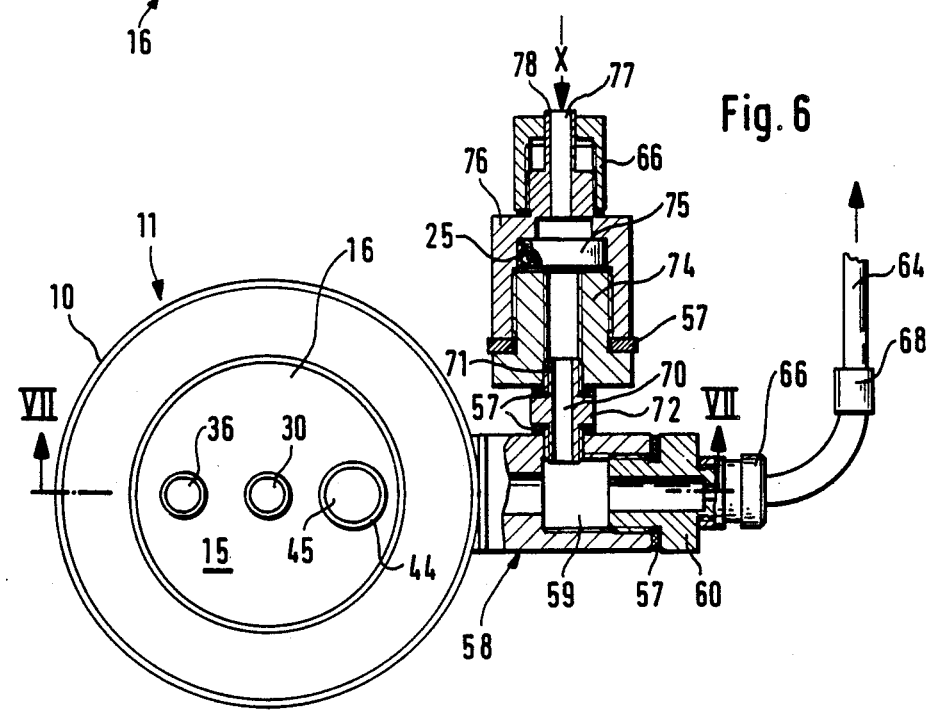

METHOD AND APPRATUS FOR MOVING A GRANULATE MATERIAL IN A DENTAL PRACTICE SITUATION

BACKGROUND OF THE INVENTION

The invention relates generally to a method of moving a granulate-like material for the treatment of a dental item such as artificial dentures or a dental prosthesis, and an apparatus for performing such a method.

In situations such as in dental laboratories there is frequently a need for small amounts of very fine-grain granulate-like material such as ceramic particles, quartz grains and the like, to be supplied under a certain pressure to the dental prosthesis or like item being handled.

SUMMARY OF THE INVENTION

An object of the present invention is to provide a method of moving a granulate material for the treatment of a dental prosthesis, which operates with a high level of operational reliability and a low level of expenditure.

Another object of the present invention is to provide a method of moving a granulate material for the treatment of dental prostheses which provides for delicate control and accuracy in the feed of the material.

Still another object of the present invention is to provide a method of moving granulate material for use in the treatment of a dental item which exhibits a high level of flexibility of use and versatility.

Yet another object of the present invention is to provide an apparatus for moving a granulate-like material for use in dealing with dental prostheses, which is easy to operate while being highly effective.

A further object of the present invention is to provide an apparatus for moving a granulate material for use in dealing with dental prostheses, which can provide a delicate and accurate control of the feed of material, even over long distances to the point of use.

In accordance with the present invention these and other objects are achieved by a method of moving a granulate-like auxiliary material for use in the treatment of a dental item such as artificial dentures or a dental prosthesis, wherein the granulate material is mixed with compressed air and is fed in a mixed jet to the article being treated thereby.

In one form of the method, the supply of compressed air or working air is effected in such a way that the granulate is fluidized by means of the compressed air and then the flowing mixture is conveyed away by means of that air.

In another feature of the invention, the method provides that a stream of control air is introduced into a container for the granular material, for fluidization thereof, while the mixture is conveyed away by working air which is only subsequently introduced into a flow conduit containing the granular material.

In regard to apparatus, the objects of the invention are achieved by an apparatus for moving a granulate-like material, for use in dealing with a dental item such as dental prostheses, comprising a container for containing the granular material, with a support base connected to the container. A riser pipe is fixed to the support base and projects into the container, extending to a level in the container above the level to which the container is filled with granular material. The riser pipe is connected, with at least one metering nozzle which terminates in the container, to an air feed means for compressed or working air, the compressed air being blown through the entire air feed means.

In another aspect of the invention the apparatus for moving a granular material for use in the treatment of a dental item such as dental prostheses comprises a container and a support base connected to the container. At least one riser pipe is fixed to the support base and extends into the container to a level above the level to which the container is filled with the granular material. The riser pipe is connected, with at least one metering nozzle which terminates in the interior of the container, to an air feed means for control air, while disposed downstream of the air feed means is an intake for the feed of compressed or working air.

Preferably, a closure member such as a squeeze or pinch valve is disposed in a discharge conduit for the discharge of the mixture of air and granulate material.

In an advantageous feature of the invention, operatively associated with the metering nozzle is a swirl or spin-effect nozzle.

By virtue of the above-indicated features, it is now possible for the granulate material in the container to be put into a form in which it is capable of flow, by virtue of a swirl effect imparted thereto by the action of the swirl nozzle, so that the material can be drawn off through the metering nozzle. In accordance with the invention the metering nozzle may have a transverse bore of a width which is preferably between 1 mm and 2.5 mm whereby grain sizes of between 25 my and 250 my can be readily transported. The two nozzles, or a plurality thereof, each terminate at a small spacing above the surface of the support base so that even when the level of material in the container is at the lowest reasonable level therein, the material can still be conveyed away by the action of the nozzles. In comparison therewith, the or each riser pipe extends upwardly into the container to a position just below the top thereof and at that location provides for a supply of air in order not to allow a reduced pressure to occur in the container. At the other end the riser pipe is connected to the air feed.

In accordance with a further preferred feature of the invention the support base is in the form of a disc portion and is air-tightly connected to the container which stands up therefrom, and the air feed means.

Extending through the disc portion transversely with respect to the longitudinal center line of the container is an air duct which is of a stepped configuration decreasing towards the longitudinal center line of the container. Thus, the stepped configuration of the air duct is provided by two outward large-diameter bores which are communicated with each other in the interior of the disc portion by a narrow bore communicating with one of the larger-diameter bores, and a further duct portion of larger diameter than the narrow bore, which is coaxial therewith and which provides a communication between the second of the larger-diameter bores and the narrow bore.

In another feature of the invention, an opening for accommodating the spin-effect or swirl nozzle extends from the above-mentioned large-diameter bore which is closest to the air intake of the arrangement, to the surface of the support base; the spin-effect or swirl nozzle comprises a tube defining a space therewithin of comparatively great width, with lateral narrow nozzle holes through which the air passes into the material which is to be put into a flowing condition. Disposed in the interior of the swirl nozzle is a filter element in order to help to check contamination of the air passages.

A further advantageous feature of the invention provides that extending from the above-mentioned large-diameter bore which is remote from the air intake of the arrangement, and substantially in rightangled relationship thereto, is a lateral arm or branch which joins to the riser pipe while an opening for accommodating the metering nozzle extends from the passage parallel to the lateral arm or branch. The free length of the riser pipe is preferably greater than ten times the free length of the swirl nozzle and/or the metering nozzle, both of which, as stated above, terminate close to the surface of the support base in order to be able to pick up material in the container even when it is at a low level therein. The diameter of the riser pipe approximately corresponds to half the free length of the metering nozzle. The latter is a tube with at least one radial transverse bore which is disposed adjacent to the free end of the tube and which is open at both ends. The diameter of the transverse bore is preferably between 1 and 2.5 mm.

In the above-defined construction of the apparatus according to the invention, which involves a feed of working air, downstream of the container, it has been found advantageous for a hose connecting pipe for the discharge to be fitted into the above-mentioned large-diameter bore which is remote from the intake for the control air, with the hose connecting pipe being provided with an inlet for the working air. Fitted into the hose connecting pipe is a screw-in portion which passes through the wall thereof and arranged thereon is a screw bush with a screw cap through which air passes.

It has been found that when the material for the dental operation is of large grain sizes, the swirl nozzle can remain out of operation, that is to say only the metering nozzle and the riser pipe are of significance in regard to conveying the material. The apparatus according to the invention which can be handled easily and without difficulties can readily supply the above-described granulate material to the laboratory station of a dental technician, even over a substantial distance.

Further objects, features and advantages of the invention will be apparent from the following description of preferred embodiments thereof.

BRIEF DESCRIPTION OF THE DRAWINGS

FIG. 6 is a partly sectional plan view of a second embodiment of the apparatus according to the invention, and FIG. 7 is a view in longitudinal section of part of the apparatus shown in FIG. 6 taken along line VII—VII in FIG. 6.

DESCRIPTION OF THE PREFERRED EMBODIMENTS

Figure 1:
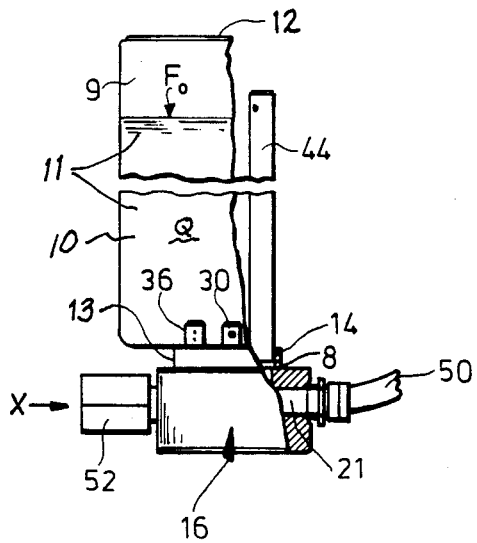
FIG. 1 is a partly sectional side view of an embodiment of the apparatus according to the invention.

Referring firstly to FIG. 1, illustrated therein is an apparatus for moving granulate-like auxiliary material for dental practice, comprising a container 11 which may be made of plastic material or light metal or alloy. The container 11 has an almost cylindrical wall as indicated at 10 which extends conically upwardly at an angle of about 2°. The container 11 has a top cover or lid 12 and it is screwed by means of a collar 13 to a screwthreaded connection portion 14 on a support base 16.

Figure 2:
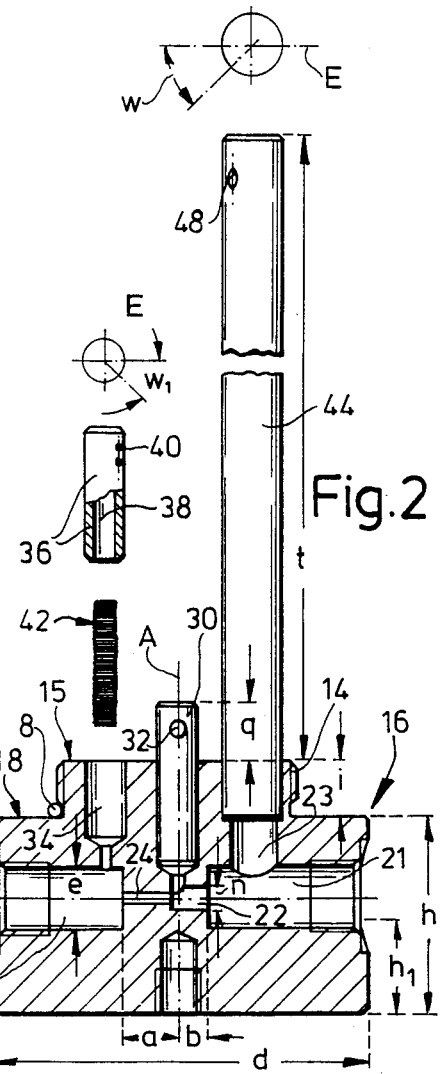
FIG. 2 is a view in longitudinal section through a part of the FIG. 1 apparatus, on a larger scale.

The support base 16 is in the form of a disc portion comprising plastic material or light metal or alloy, of a diameter as indicated at d in FIG. 2 of about 50 mm, while the height thereof, as indicated at h in FIG. 2, is for example 35 mm. The screwthreaded connecting portion 14 projects from an annular surface 18 on the support base 16, to a height as indicated at i in FIG. 2, of about 7.5 mm.

Referring now more specifically to FIG. 2, mounted slightly above a plane defined by half the base heightwise dimension as indicated by $h_1$, at a diameter D of the support base 16, are two mutually oppositely disposed large-diameter, substantially blind bores 20 and 21 which are of a diameter as indicated by e in FIG. 2 of 8.5 mm in this embodiment. The bores 20 and 21 terminate at different spaces a, b (for example 7.25 mm and 3.75 mm respectively) from the longitudinal center line A of the container 11. From the bore 21 a coaxial passage 22 of a diameter n of 3 mm extends slightly beyond the longitudinal center line A of the container 11 and is communicated with the other bore 20 by way of a bore 24 of about half the diameter n of the passage 22.

Reference numeral 26 in FIG. 2 denotes thin filter inserts for fitting into the bore 20, while reference numeral 27 denotes a thick filter insert with which a screen or sieve member 28 is associated.

Figure 3:
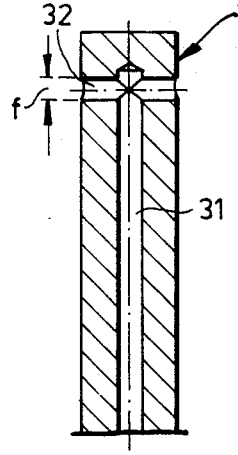
FIGS. 3 through 5 are views in longitudinal section through parts of the apparatus shown in FIGS. 1 and 2.

Extending on the longitudinal center line A of the container 11 is an opening or recess which is identified at 17 in FIG. 7 but which is not specifically referenced in FIG. 2, in the support base 16. The opening 17 accommodates a central tube acting as a metering nozzle 30 with a bore configuration 31, 32 of generally T-shaped configuration. The bore configuration 31, 32 can be clearly seen in the sectional view in FIG. 3. The diameter f of the transverse bore 32 which opens at both sides of the metering nozzle 30 is 1.2 mm, in the embodiment described by way of example. The metering nozzle 30 projects about 10 mm, as indicated at q in FIG. 2, from the surface 15 of the screwthreaded connecting portion 14 on the support base 16.

Figure 4:
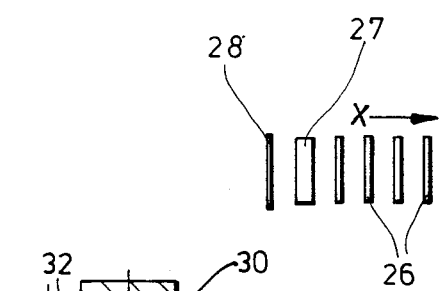

The support base 16 is provided also with a cylindrical opening 34 which extends parallel to the axis A and which is connected to the bore 20 shown at the left in FIG. 2. Fitted in the opening 34 is a swirl or spin-effect nozzle 36 which is in the form of a tube and which defines an axial passage 38 therein. Two narrow nozzle holes 40 which are shown in greater detail in FIG. 4 and which are each of a diameter indicated at s in FIG. 4 of 0.5 mm in this embodiment extend in mutually parallel relationship from the passage 38 in the nozzle 36. A filter insert indicated at 42 in FIG. 2 is disposed in the passage 38.

On the other side of the metering nozzle 30 from the swirl nozzle 36, a riser pipe 44 is mounted on the support base 16, in parallel relationship with the nozzles 30 and 36. The riser pipe 44 has a free height as indicated at t in FIG. 2 of about 140 mm in this embodiment. The riser pipe 44 is connected downwardly to a lateral arm or branch 23 extending from the bore 21, and is therefore communicated therewith.

Figure 5:
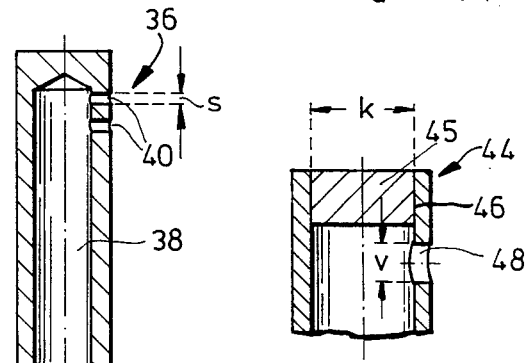

While the two nozzle tubes 30 and 36 each comprise a bored-out non-ferrous metal rod, the riser pipe 44 is preferably produced from an aluminum alloy by an extrusion operation, with a comparatively large inside diameter k of about 6 mm. The head end of the riser pipe 44 is closed by a disc portion 45 (as shown in FIG. 5), which is secured to the riser pipe 44 for example by adhesive as indicated at 46 in FIG. 5. Provided in the riser pipe 44 a little below the disc portion 45 is a lateral hole 48 of a diameter v of somewhat more than 2 mm.

FIG. 2, above the top end of the riser pipe 44, indicates that each hole 48 therein is disposed at an angle w of about 45° relative to a central plane E. The nozzle holes 40 in the nozzle 36 are also disposed at such an angle $w_1$ relative to the plane E, with the two angles w and $w_1$ being directed towards each other, as can be clearly seen from FIG. 2. The transverse bore 32 of the metering nozzle 30 extends perpendicularly to the plane E.

For use in a dental laboratory situation, the container 11 is filled for example with a quartz granulate material as indicated at Q of a grain size of from 25 to 50 my. A possible upper filling level in the interior 7 of the container is indicated at $F_0$ in FIG. 1. When compressed air acting as working air passes into the bore 20 as indicated by the arrow X in FIGS. 1 and 2, then, by virtue of the swirl nozzle 36, fluidization of the granulate material Q in the container 11 begins. The fluidized material Q passes through the transverse bore 32 and the communicating axial bore 31 in the metering nozzle 30 into the passage 22 and flows from the passage 22 into the bore 21 at the right in FIG. 2. Connected to the bore 21 in FIG. 1 is a conveyor hose 50 for the air/granulate mixture. The oppositely disposed air feed connection is identified by reference numeral 52 in FIG. 1.

By virtue of the riser pipe 44 which extends into the space 9 above the level to which the container 11 is filled with granulate material Q, the space 9 can be readily vented so that a reduced pressure which would impede transportation of the granulate material Q out of the container 11 cannot occur in the space 9.

The filters 42, 26 and 27 prevent or at least retard contamination or clogging of the air feed components 52 and 38.

A screwthreaded hole 53 in the support base 16 serves for securing the apparatus to a mounting plate or the like which is not shown in the drawing for the sake of clarity thereof.

The entire apparatus is sealingly closed, for example by virtue of an O-ring 8 being arranged between the container 11 and the support base 16, so that pressure conveyance of the granulate material Q to the dental item such as artificial dentures or a dental prosthesis or the like, which is to be subjected to treatment with the material Q, is readily possible in a simple fashion, with safe handling.

In a construction which is not illustrated herein for use with granulate material Q of larger grain size, for example 100 to 250 my, the swirl nozzle 36 does not come into operation; as in the case of the embodiment illustrated, the compressed air which is supplied to the apparatus passes out of the bore 20 and by way of the axial bore 24 into the passage 22, granulate material Q being drawn in through the transverse bores 32 and the axial bore 31 in the metering nozzle 30 and being fed to the bore 21 for discharge thereof.

Referring now to FIGS. 6 and 7, in the construction illustrated therein a screw connection 56 of a hose connecting pipe 58 is fitted into the bore 21. The hose 58 is connected to the screw connection 56, with the interposition of a sealing ring as indicated at 57. The space 59 within the screw connection 56 is closed at the end remote from the bore 21 by a closure nut 60 which in turn is screwed into the screw connection 56 and which is provided with a coaxial mouth portion 62 for connection of a flexible line as indicated at 64 in FIG. 6. The line 64 is held in position by a cap nut 66 and has a shut-off member indicated at 68 for example in the form of a squeeze or pinch valve.

Transversely with respect to the diameter D of the support base 16, opening into the interior 59 of the hose 58 is the bore 70 of a tubular screw-in portion which is indicated generally by reference numeral 71 in FIG. 6, with a nut-like central collar portion 72. At the other end the portion 71 is fitted into a screw bush or sleeve 74 which carries a screw cap 76, thereby forming a receiving space 75 for filter inserts as indicated at 25. The space 75 in the screw bush or sleeve 74 communicates with an axial bore 77 of a hose connecting end 78 which is formed thereon. A cap nut 66 is also associated with the connecting end 78.

In this embodiment, control air is blown in through the air connection 52 whereas the conveying or working air required is introduced through the bore 70. Mixing of the working air and the granulate material occurs in this embodiment in the space 59 in the hose connecting tube 58. The flow of material being conveyed can be readily interrupted by means of the squeeze valve 68.

The remainder of the construction of the apparatus shown in FIGS. 6 and 7 is generally similar to that described above with reference to FIGS. 1 through 5 and will therefore not be described again at this point.

It will be appreciated that the above-described constructions have been set forth solely by way of example and illustration of the present invention and various modifications and alterations may be made therein without thereby departing from the spirit and scope of the present invention.

What is claimed is:

1. Apparatus for moving a granulate material for use on dental prosthesis items comprising a container having an interior portion for said material, a support base means connected to the container, duct means for carrying a flow of compressed working air in said support base means, at least one riser pipe fixed to the support base means and projecting into the container to a level above the level of material which in use of the apparatus is contained in the container for venting the interior of said container, means connecting the riser pipe to said duct means, at least one metering nozzle which terminates in the interior of the container and which is connected to said duct means, said metering nozzle extending into the container and having an inlet in the interior thereof for receiving said granulate material, including a recess means extending in substantially right angle relationship to said duct means for accommodating said metering nozzle, thereby to carry a flow of said material from said container into said duct means, and further comprising at least one swirl nozzle with an axial passage therein having at least one opening to the interior of said container associated with said metering nozzle, connected to said duct means, and terminating in the interior of the container for feeding air to the granulate material in the container.

2. Apparatus as set forth in claim 1 wherein said support base means is a disc portion and is air-tightly connected to the container which stands up therefrom, and an air feed means is connected to said duct means.

3. Apparatus as set forth in claim 1 wherein said duct means includes a passage extending through said support base means transversely with respect to a longitudinal center line of the container and wherein said passage is of a stepped configuration which decreases towards said center line from respective ends thereof.

4. Apparatus as set forth in claim 3 including an air inlet of said duct means and wherein said passage comprises first and second outwardly disposed bores, and wherein the one bore which is closest to the air inlet of the duct means is connected by a narrow bore portion to a coaxial passage portion of larger diameter which extends from the inward end of the other said bore.

5. Apparatus as set forth in claim 4 and further comprising a lateral branch duct portion which joins said riser pipe and which extends in substantially right-angled relationship from said other bore.

6. Apparatus as set forth in claim 4 and further comprising a recess means which extends in substantially right-angled relationship from said passage portion, for accommodating said metering nozzle.

7. Apparatus as set forth in claim 4 and further comprising an opening for accommodating said swirl nozzle, said opening extending from said one bore to the surface of said support base means.

8. Apparatus as set forth in claim 1 wherein the free-length of said riser pipe is greater than ten times the free length of the metering nozzle.

9. Apparatus as set forth in claim 1 wherein the free length of said riser pipe is greater than ten times the free length of the swirl nozzle.

10. Apparatus as set forth in claim 1 wherein the diameter of the riser pipe approximately corresponds to half the free length of the metering nozzle.

11. Apparatus as set forth in claim 1 wherein the metering nozzle is a tube portion with at least one radial transverse bore which is adjacent to the free end thereof and which is open at both ends.

12. Apparatus as set forth in claim 11 wherein said at least one transverse bore is of a diameter of from 1 to 2.5 mm.

13. Apparatus as set forth in claim 1 wherein said swirl nozzle has an axial passage and is provided adjacent its free end with at least one substantially needle-size nozzle hole.

14. Apparatus as set forth in claim 13 wherein the diameter of said further axial passage is substantially 3 to 4 mm.

15. Apparatus a set forth in claim 13 including at least one filter means disposed in the axial passage of said swirl nozzle.

16. Apparatus as set forth in claim 1 and further comprising at least one filter disposed in the duct means.

17. Apparatus for moving a granulate material for use on dental prosthesis items comprising a container having an interior portion for containing said material, a support base means connected to the container, duct means for carrying a flow of control air in said support base means, at least one riser pipe fixed to the support base means and projecting into the container to a level above the level of material which in use is contained in the container for venting the interior of said container, means connecting the riser pipe to said duct means, at least one metering nozzle which terminates in the interior of the container and which is connected to said duct means, said metering nozzle extending into the container and having an inlet in the interior thereof for receiving said granulate material, thereby to carry a flow of said material from said container into said duct means, including a recess means extending in substantially right angle relationship to said duct means for accommodating said metering nozzle, and an intake for compressed working air into the apparatus downstream of said duct means, and further comprising at least one swirl nozzle with an axial passage therein having at least one opening to the interior of said container associated with said metering nozzle, connected to said duct means, and terminating in the interior of the container for feeding air to the granulate material in the container.

18. Apparatus as set forth in claim 17 and further including a discharge conduit for the mixture of working air and granulate material, and at least one closure member on said discharge conduit.

19. Apparatus as set forth in claim 18 wherein said closure member is a pinch valve.

20. Apparatus as set forth in claim 17 wherein said support base means is a disc portion and is air-tightly connected to the container which stands up therefrom, and an air feed means is connected to said duct means.

21. Apparatus as set forth in claim 17 wherein said duct means includes a passage extending through said support base means transversely with respect to a longitudinal center line of the container and wherein said passage is of a stepped configuration which decreases towards said center line.

22. Apparatus as set forth in claim 21 including an air inlet of said duct means and wherein said passage comprises first and second outwardly disposed bores and wherein the one bore which is closer to the air inlet of the duct means is connected by a narrow bore portion to a coaxial passage portion of larger diameter which extends from the inward end of the other said bore.

23. Apparatus as set forth in claim 22 and further comprising an opening accommodating said swirl nozzle, said opening extending from said one bore to the surface of said support base means.

24. Apparatus as set forth in claim 22 and further comprising a lateral branch duct joining said riser pipe and extending substantially perpendicularly from the said other bore.

25. Apparatus as set forth in claim 22 and further including a recess means extending substantially perpendicularly from said passage portion, to accommodate said metering nozzle.

26. Apparatus as set forth in claim 17 wherein the free length of said riser pipe is greater than ten times the free length of the metering nozzle.

27. Apparatus as set forth in claim 17 wherein the free length of said riser pipe is greater than ten times the free length of the swirl nozzle.

28. Apparatus as set forth in claim 17 wherein the diameter of the riser pipe approximately corresponds to half the free length of the metering nozzle.

29. Apparatus as set forth in claim 17 wherein said metering nozzle is a tube portion having at least one radially extending transverse bore adjacent to the free end of the tube portion, the transverse bore being open at both ends.

30. Apparatus as set forth in claim 29 wherein said at least one transverse bore is of a diameter of from 1 to 2.5 mm.

31. Apparatus as set forth in claim 17 wherein said swirl nozzle has a on axial passage and is provided adjacent its free end with at least one substantially needle-size nozzle hole.

32. Apparatus as set forth in claim 31 wherein the diameter of said further axial passage is substantially 3 to 4 mm.

33. Apparatus as set forth in claim 31 including at least one filter means disposed in the axial passage of said swirl nozzle.

34. Apparatus as set forth in claim 17, and further comprising a hose connecting tube for the discharge, said tube being fitted into a bore of said duct means which is remote from said control air inlet, said hose connecting tube being provided with said intake for said compressed working air.

35. Apparatus as set forth in claim 17 and further comprising at least one filter disposed in said duct means.

36. Apparatus as set forth in claim 35 and further comprising fitted radially into said hose connecting tube a screw-in portion which passes through the wall thereof and disposed on said screw-in portion a screw bush having a screw cap with air passage therethrough.

37. Apparatus for moving a granulate material for use on dental prosthesis items comprising a container for said material, a support base means connected to the container, duct means for carrying a flow of compressed working air in said support base means, at least one riser pipe fixed to the support base means and projecting into the container to a level above the level of material which in use of the apparatus is contained in the container, means connecting the riser pipe to said duct means, and at least one metering nozzle which terminates in the interior of the container and which is connected to said duct means, including a recess means extending in substantially right angle relationship to said duct means for accommodating said metering nozzle, thereby to carry a flow of said material from said container into said duct means, wherein the metering nozzle is a tube portion with at least one radial transverse bore which is adjacent to the free end thereof and which is open at both ends, and wherein said riser pipe has a lateral hole adjacent its end and extending at an angle relative to the transverse bore of said metering nozzle.

38. Apparatus as set forth in claim 37, wherein said angle is substantially 45°.

39. Apparatus for moving a granulate material for use on dental prosthesis items comprising a container for said material, a support base means connected to the container, duct means for carrying a flow of compressed working air in said support base means, at least one riser pipe fixed to the support base means and projecting into the container to a level above the level of material which in use of the apparatus is contained in the container, means connecting the riser pipe to said duct means, and at least one metering nozzle which terminates in the interior of the container and which is connected to said duct means, including a recess means extending in substantially right angle relationship to said duct means for accommodating said metering nozzle, thereby to carry a flow of said material from said container into said duct means, and further comprising a swirl nozzle associated with said metering nozzle, wherein said swirl nozzle has an axial passage and is provided adjacent its free end with at least one substantially needle-size nozzle hole, and wherein said metering nozzle includes at least one radial transverse bore which is adjacent the free end thereof, and wherein said nozzle hole in the swirl nozzle extends at an angle relative to the transverse bore of said metering nozzle.

40. Apparatus as set forth in claim 39, wherein said angle is substantially 45°.

41. Apparatus for moving a granulate material for use on dental prosthesis items comprising a container for containing said material, a support base means connected to the container, duct means for carrying a flow of control air in said support base means, at least one riser pipe fixed to the support base means and projecting into the container to a level above the level of material which in use is contained in the container, means connecting the riser pipe to said duct means, at least one metering nozzle which terminates in the interior of the container and which is connected to said duct means thereby to carry a flow of said material from said container into said duct means, including a recess means extending in substantially right angle relationship to said duct means for accommodating said metering nozzle, and an intake for compressed working air into the apparatus downstream of said duct means wherein said metering nozzle is a tube portion having at least one radially extending transverse bore adjacent to the free end of the tube portion, the transverse bore being open at both ends, and wherein said riser pipe has a lateral hole adjacent its end and extending at an angle relative to the transverse bore of said metering nozzle.

42. Apparatus as set forth in claim 41, wherein said angle is substantially 45°.

43. Apparatus for moving a granulate material for use on dental prosthesis items comprising a container for containing said material, a support base means connected to the container, duct means for carrying a flow of control air in said support base means, at least one riser pipe fixed to the support base means and projecting into the container to a level above the level of material which in use is contained in the container means connecting the riser pipe to said duct means, at least one metering nozzle which terminates in the interior of the container and which is connected to said duct means thereby to carry a flow of said material from said container into said duct means, including a recess means extending in substantially right angle relationship to said duct means for accommodating said metering nozzle, and an intake for compressed working air into the apparatus downstream of said duct means and further comprising a swirl nozzle associated with said metering nozzle wherein said swirl nozzle has an axial passage and is provided adjacent its free end with at least one substantially needle-size nozzle hole, wherein said metering nozzle includes at least one radial transverse bore which is adjacent the free end thereof, and wherein said nozzle hole in the swirl nozzle extends at an angle relative to the transverse bore of said metering nozzle.

44. Apparatus as set forth in claim 43, wherein said angle is substantially 45°.

* * * * *